(12) United States Patent
Taranow

(10) Patent No.: US 7,611,476 B2
(45) Date of Patent: Nov. 3, 2009

(54) VACUUM-SEALED ORTHOTIC, PROSTHETIC, AND OTHER BODY WORN DEVICES

(76) Inventor: Warren S. Taranow, 2550 Devonshire, Ann Arbor, MI (US) 48104

( * ) Notice: Subject to any disclaimer, the term of this patent is extended or adjusted under 35 U.S.C. 154(b) by 626 days.

(21) Appl. No.: 10/791,948

(22) Filed: Mar. 3, 2004

(65) Prior Publication Data
US 2005/0197611 A1 Sep. 8, 2005

(51) Int. Cl.
A61F 5/00 (2006.01)

(52) U.S. Cl. .............. 602/16; 602/12; 602/13; 602/14; 602/6; 602/26; 602/27

(58) Field of Classification Search ......... 602/6, 602/12, 13, 14, 26, 27; 224/171, 219, 221, 224/222; 206/524.8; 383/100, 103; 606/201, 606/202
See application file for complete search history.

(56) References Cited

U.S. PATENT DOCUMENTS

| | | | |
|---|---|---|---|
| 2,696,011 A | 12/1954 | Galdik | |
| 2,808,593 A | 10/1957 | Andersen | |
| 4,479,272 A | 10/1984 | Beldzisky | |
| 4,657,003 A * | 4/1987 | Wirtz | 128/869 |
| 4,768,501 A | 9/1988 | George | 128/82 |
| 4,822,371 A | 4/1989 | Jolly et al. | |
| 4,908,037 A | 3/1990 | Ross | |
| 5,253,435 A | 10/1993 | Auger et al. | 36/88 |
| 5,376,131 A | 12/1994 | Lenze et al. | 623/34 |
| 5,399,152 A * | 3/1995 | Habermeyer et al. | 602/23 |
| 5,472,413 A * | 12/1995 | Detty | 602/26 |
| 5,520,622 A | 5/1996 | Bastyr et al. | |
| 5,542,911 A | 8/1996 | Cassford et al. | |
| 5,573,501 A * | 11/1996 | Ruscito et al. | 602/7 |
| 5,593,454 A | 1/1997 | Helmy | |
| 5,718,669 A * | 2/1998 | Marble | 602/5 |
| 5,797,865 A * | 8/1998 | McDavid, III | 602/27 |
| 5,865,772 A | 2/1999 | George | |
| 6,287,345 B1 | 9/2001 | Slemker et al. | |
| 6,397,400 B1 * | 6/2002 | Hassler et al. | 2/455 |
| 6,402,711 B1 * | 6/2002 | Nauert | 602/16 |
| 6,406,499 B1 | 6/2002 | Kania | |
| 6,554,868 B1 | 4/2003 | Caspers | |
| 6,645,253 B2 | 11/2003 | Caspers | |
| 6,726,726 B2 | 4/2004 | Caspers | |
| 6,761,742 B2 | 7/2004 | Caspers | |
| 7,144,429 B2 | 12/2006 | Carstens | |
| 7,169,188 B2 | 1/2007 | Carstens | |
| 2001/0020143 A1 * | 9/2001 | Stark et al. | 602/13 |
| 2002/0052568 A1 * | 5/2002 | Houser et al. | 602/26 |

* cited by examiner

Primary Examiner—Patricia Bianco
Assistant Examiner—Tarla Patel
(74) Attorney, Agent, or Firm—Gifford, Krass, Sprinkle, Anderson & Citkowski, P.C.

(57) ABSTRACT

Active suctioning is used to evacuate a fabric, film or membrane for the purpose of securing orthotic, prosthetic, or other body worn articles, including sports-related articles. In contrast to the straps and tight-fitting approaches of existing devices, the inventive methods and apparatus provide for a slip-free seal to surrounding body parts, thereby simplifying construction, reducing weight, and enhancing comfort. The invention is applicable to any type of orthosis, prosthesis, foot wear, mitts, gloves, and so forth, including apparatus associated with the ankle and foot, knee, hip, back and neck, shoulder, elbow and hand.

9 Claims, 7 Drawing Sheets

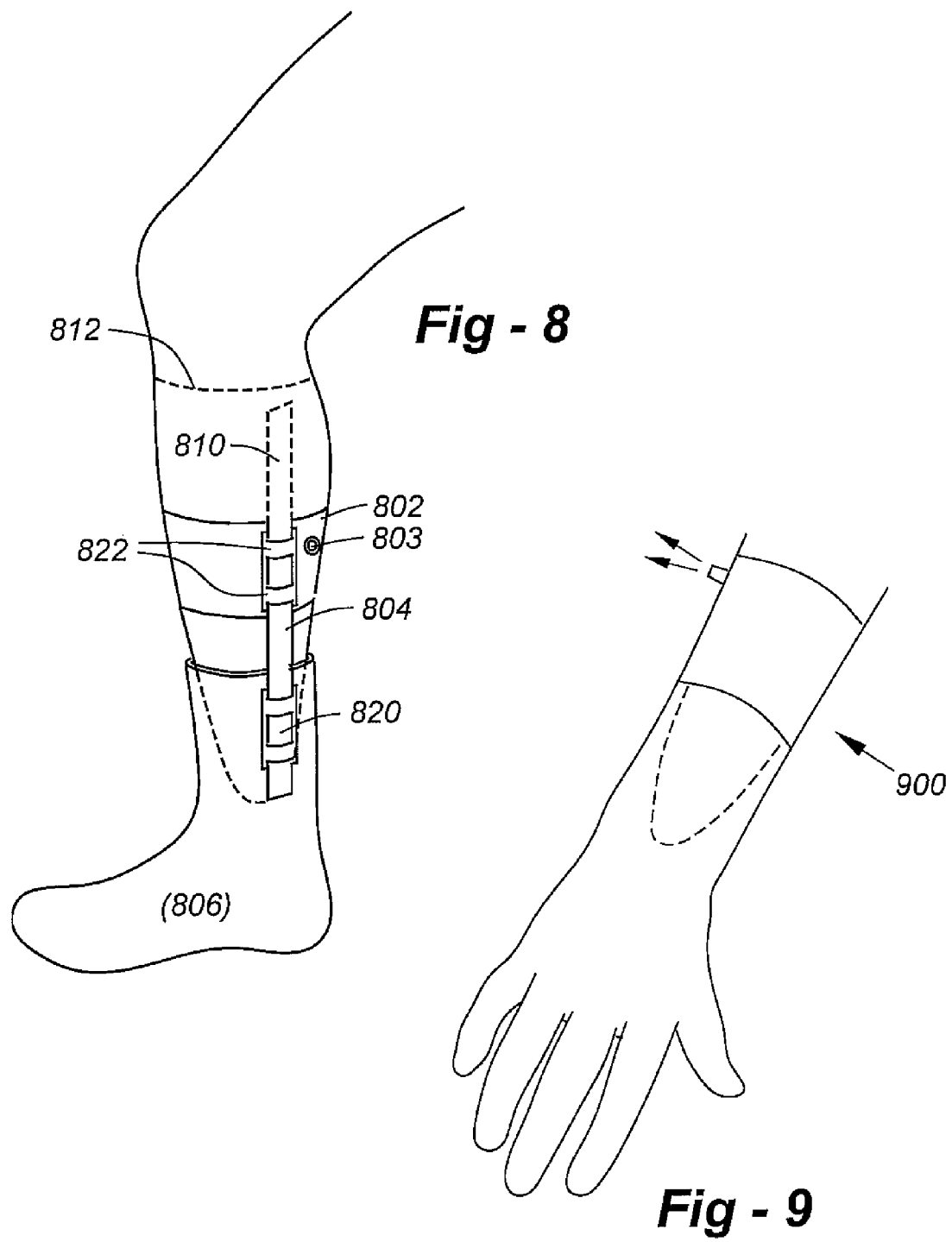

VACUUM-SEALED ORTHOTIC, PROSTHETIC, AND OTHER BODY WORN DEVICES

FIELD OF THE INVENTION

This invention relates generally to body worn appliances and, in particular, to orthotic, prosthetic, and other devices that are held in position using active suctioning.

BACKGROUND OF THE INVENTION

When attaching items to the human body, such as prosthetic orthotic appliances, it is desirable to have an accurate fit to optimize results and reduce discomfort. The same holds true for shoes, gloves and other sports-related items.

FIG. 1 is a drawing that shows a typical orthopedic brace designed for the knee. The device, shown generally at 100, includes an upper portion 102 secured to the area above the knee joint 108, and a lower portion 104 secured below the knee. To control appropriate range of motion, hinges 103, 106 are provided on the lateral and medial sides, and these hinges connect to stiff bars 110, 112, which are secured with Velcro® straps 120, 122, which are tightened around the leg. The hinges 103, 106 may include gages and guides to increase and decrease range of motion, depending upon the condition of the wearer.

Apart from the appliance of FIG. 1 being heavy, bulky, and generally expensive, the general concept of securing devices of this kind to the leg or other appendage utilizing straps simply does not work. Due to the weight and location of the device, during walking in particular, it slips down, causing the axes of the hinges 103, 106 to fall, thereby effectively defeating the overall effectiveness of the product. In addition, the bulk of the unit tends to cause the wearer to don the appliance over one's clothing, exacerbating the problem with loosening and misalignment.

Particularly with respect to prosthetic devices such as artificial limbs, it has been recognized that suction may be advantageously used to hold the appliance in position. As discussed in U.S. Pat. No. 5,376,131, artificial limbs using suction sockets are in widespread use today. These sockets are provided with a one-way air valve so that, on placing the stump of the patient's leg into the socket, the air is expelled from the interior of the socket to the outside, thus creating a partial vacuum in the airspace between the patient's stump and the interior of the socket. The difference in pressure between the atmospheric air outside the socket and the vacuum within the socket holds the socket in place until air is readmitted to the socket by opening the one-way valve.

A major pitfall of the suction socket is the inability to provide an effective seal at the proximal open end of the socket. Even if the socket is perfectly fitted to the patient's stump, the stump will contract or shrink during the course of the day, thereby permitting air to leak into the socket, thereby reducing and in some cases completely eliminating the differential air pressure between the atmospheric air outside the socket and the airspace between the patient's stump and the socket. A variety of techniques have been adopted to address this problem, such as providing the patient with special socks to accommodate for this shrinkage. However, in practice, the patient must remove the prosthesis to apply the sock as suction is lost during the day, which is certainly inconvenient.

Another attempt to address this problem is the provision of auxiliary suspension devices, such as belts or the like, to hold the socket in place during the course of the day. This simply adds to the weight and bulk of the prosthesis and does not address the cause of the problem, namely the loss of suction due to shrinkage of the patient's stump.

The invention of the '131 patent solves this problem through the provision of a self-adjusting sealing member adjacent the proximal open end of the suction socket adapted to maintain the seal between the proximal open end of the socket and the patient's stump as the stump shrinks during the course of the day.

Inflation, as opposed to suction, has for years been used to improve the fit of athletic shoes such as running shoes. To reference one patent of many, U.S. Pat. No. 5,253,435 teaches a bladder assembly for an athletic shoe and having at least first and second chambers. The chambers are independently and separately pressure adjustable by the user to conform to different concavity areas of his foot, such as the arch, ankle and metatarsal areas, to thereby enhance fit, comfort and athletic performance. Both chambers are inflatable by the same articulated on-board pump and deflatable by the same on-board depressible plunger. A dial on the lateral side of the upper allows the user to select which of the chambers is to be pressure adjusted, that is, which of the chambers is in pressure communication with the pump and the plunger. When the dial is in a neutral position, accidental inflation or deflation of either chamber is prevented.

Active evacuation has been used with respect to materials that make skin contact, but only for the purpose of waterproofing. U.S. Pat. No. 4,768,501, for example, comprises a method of waterproof sealing a patient's cast or dressing through the use of a water- and air-impervious flexible membrane. The method includes the steps of placing the membrane over the cast or dressing so that the membrane's edge margin extends over a portion of the patient's skin along a perimeter of the cast or dressing. In the next step a vacuum is formed between the membrane and cast or dressing sufficient to cause atmospheric pressure to force the membrane into sealing contact with the skin and with a snug, close fit with the cast or dressing. In one embodiment the vacuum is formed by inserting a suction tube through the interface between the membrane edge margin and skin and evacuating air through the tube. After the sealing contact between the membrane and skin is formed the suction tube is withdrawn. In another embodiment the vacuum is formed by evacuating air through an air valve which is provided in the membrane.

In view of these teachings, the need remains for improved articles and methods for securing prosthetic, orthotic, and sports-related equipment to the human body.

SUMMARY OF THE INVENTION

This invention improves upon the existing art through the use of active suction to evacuate a fabric, film or membrane for the purpose of securing orthotic, prosthetic, or other body worn articles, including sports-related articles. In contrast to the straps and tight-fitting approaches of existing devices, the inventive methods and apparatus provide for a slip-free seal to surrounding body parts, thereby simplifying construction, reducing weight, and enhancing comfort.

The invention is applicable to any type of orthosis, prosthesis, foot wear, mitts, gloves, and so forth, including apparatus associated with the ankle and foot, knee, hip, back and neck, shoulder, elbow and hand.

In alternative embodiments, evacuatable sleeves are used which may either provide an initial loose fit or relatively tight fit, with optional elastic bands being used on one or both ends to ensure a good vacuum. Evacuation may occur through any source, including a hand-operated bulb or plunger, including electrically operated mechanisms. The invention is not limited in this regard, nor is the invention limited in terms of the type of materials that may be used, since latex, stretchable or flexible membranes or other fabrics may be used.

If cushioning is desirable, as may be the case with a glove, mitt or shoe, the evacuatable sleeve may be disposed over or under such materials, whether provided for shock resistance, warmth, or other purposes. Devices according to the invention may or may not be attached to rigid elements or hinges, depending upon the application, and such other devices may be attached by any appropriate means, including permanent or temporary fixation, as through hook-and-loop fasteners, J-locking mechanisms or other approaches.

BRIEF DESCRIPTION OF THE DRAWINGS

FIG. 8 is a drawing that illustrates an artificial limb according to the invention, in this case, an artificial foot;

FIG. 9 is a drawing which shows an artificial hand embodiment of the invention;

DETAILED DESCRIPTION OF THE INVENTION

Figure 1:
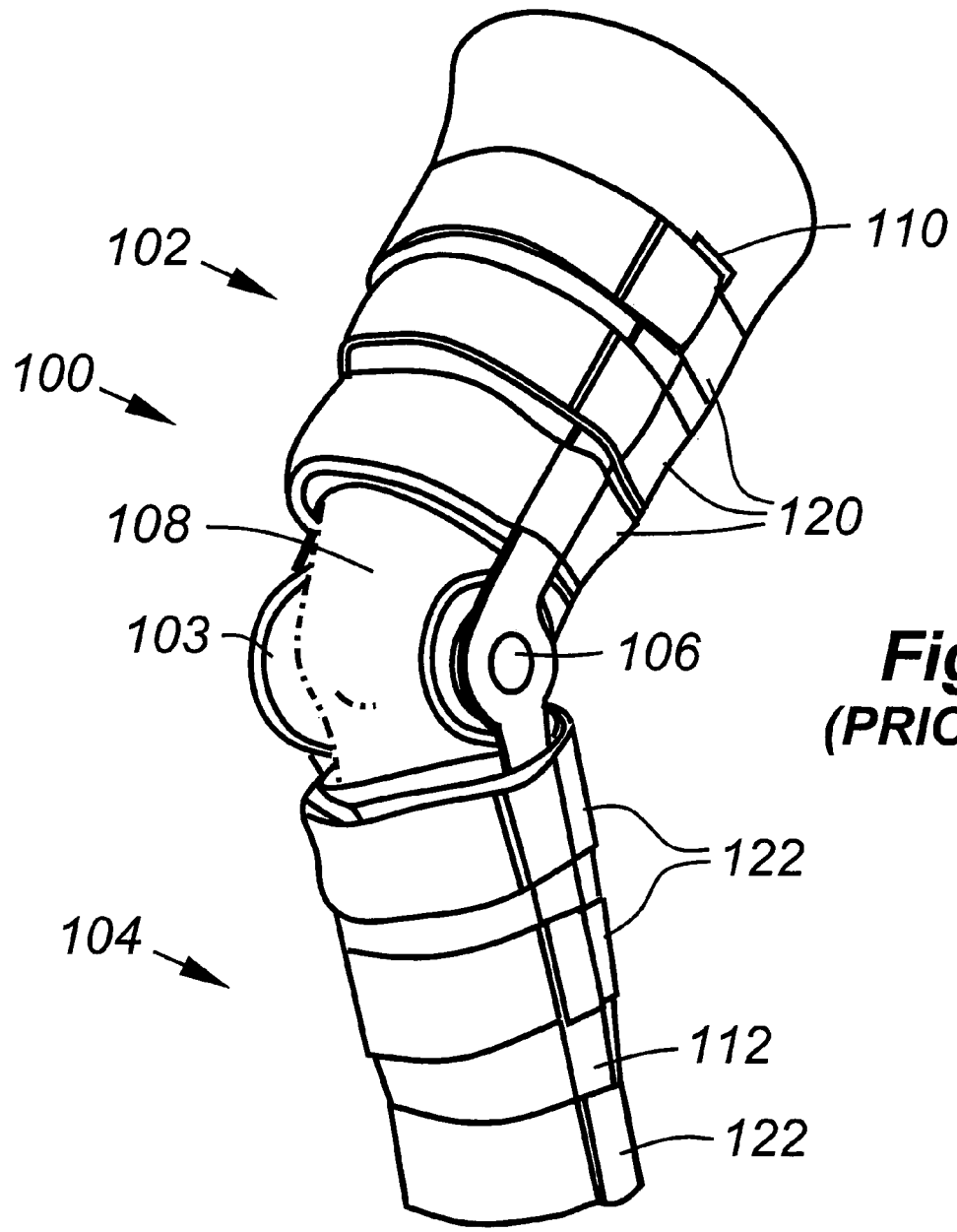
FIG. 1 is a drawing of a prior-art knee brace which utilizes straps and compression to keep it in place, often requiring repositioning.
Figure 2:
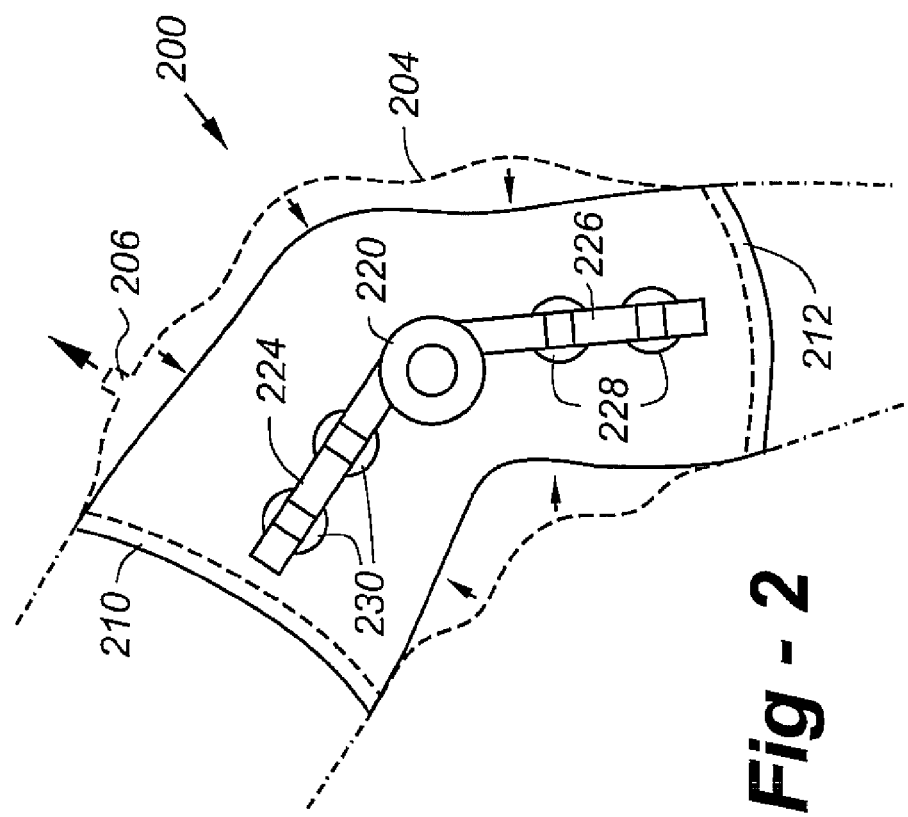
FIG. 2 is a drawing of a preferred embodiment of the invention associated with an orthotic, namely, a hinged knee brace.

Having discussed the prior-art brace of FIG. 1, the reader's attention is directed to FIG. 2, which illustrates a knee brace embodiment of the invention generally at 200. Broadly, as with other embodiments disclosed herein, the appliance incorporates a membrane 204 that is evacuatable through a port 206, causing the material to be "shrink wrap" down onto the skin, resulting in an extremely tenacious bond to the skin that resists slipping, falling and misalignment. The evacuation through port 206 may occur through any suitable means according to the invention, including manually operated bulbs or plungers, or electrically operated pumps. Although not necessary, elastic bands 210, 212 may be provided to provide an initial seal at the proximal and distal ends of the sleeve, thereby improving the suctioning process.

In the embodiment of FIG. 2, a hinged brace is attached to one or both sides of the sleeve material, though, as will be appreciated from the description of alternative embodiments below, non-hinged, i.e., stiffening members, may alternatively be utilized. In the arrangement of FIG. 2, the device includes a hinged portion 220, connected to rigid members 224, 226 which, in turn, are fastened to the material 204 through any suitable means, including permanent bonding through thermal or chemical adhesion, or temporarily through snap-type fasteners, Velcro, straps, sleeves, and the like. In the preferred embodiment, a temporary securement is used, allowing the sleeve to be placed over the appendage, evacuated for a tight fit, followed by the application of the hinged or rigid brace member.

Figure 3:
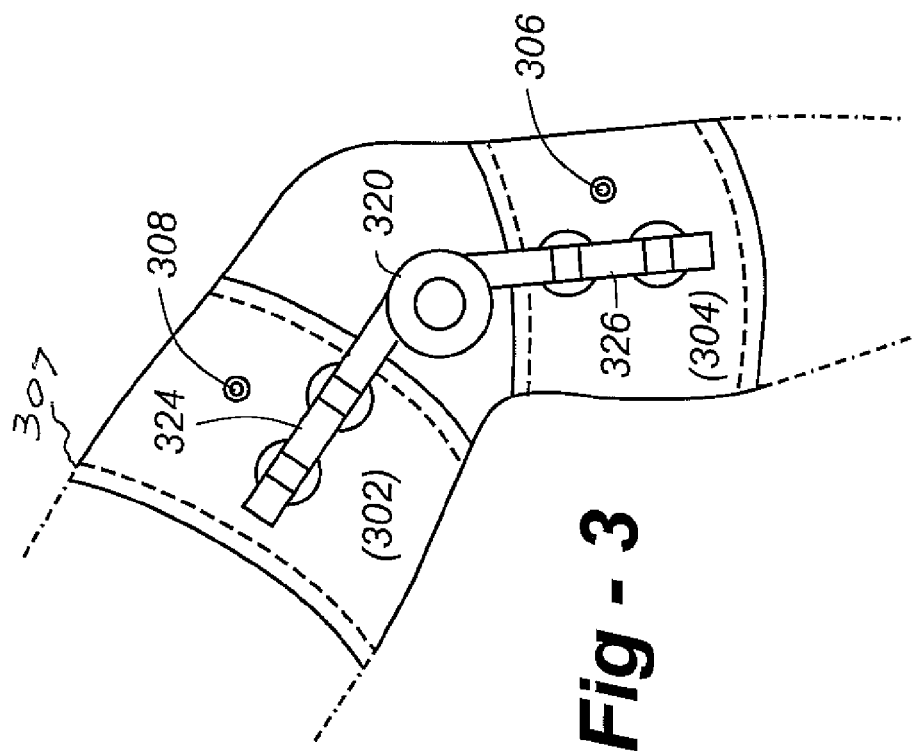
FIG. 3 is an alternative embodiment of a knee brace utilizing a pair of suction bands as opposed to a single evacuatable sleeve.

Although a single sleeve such as 204 in FIG. 2 may be used, in alternative embodiments, separate sleeves 302, 304, may be used on either side of a joint, such as the knee joint shown, or other joints such as the hip, elbow, wrist, ankle, shoulder, and so forth. In the embodiment of FIG. 3, an upper sleeve 302 is evacuated through port 308, and a lower sleeve 304 is evacuated through a separate port 306. Again, opposing bands such as 307 may be provided to assist with the evacuation process. A hinge 320 connects to rigid members 324, 326 which are adhered to the respective sleeves 302, 304 through any appropriate means as discussed with reference to FIG. 2. Additionally, though not shown, hinges such as 220, 320 may be provided with dials and gages to permit a particular range of motion, as with conventional braces.

Figure 4:
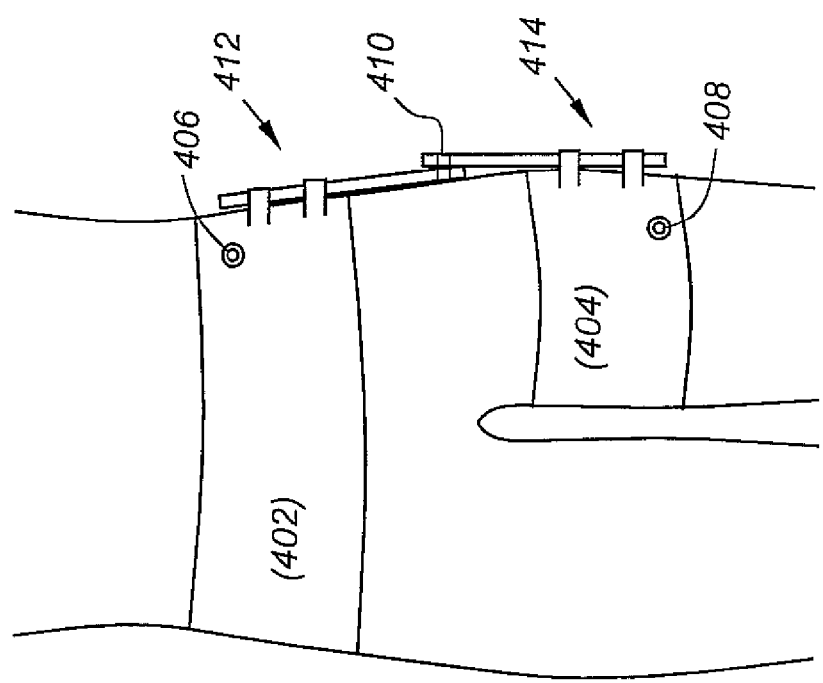
FIG. 4 is a drawing which shows a hip brace embodiment of the invention.

FIG. 4 illustrates a hip-joint embodiment of the invention, including an upper, waist-encircling band 402, evacuated a port 406, a lower band 404, evacuated through a port 408, and a hinge member 410, having an upper portion 412 adhered to the band 402 and a lower portion 414 adhered to the lower band 404. Again, though this is shown as hinged, a rigid member may be used for a more global restriction of motion, depending upon the application.

Figure 5:
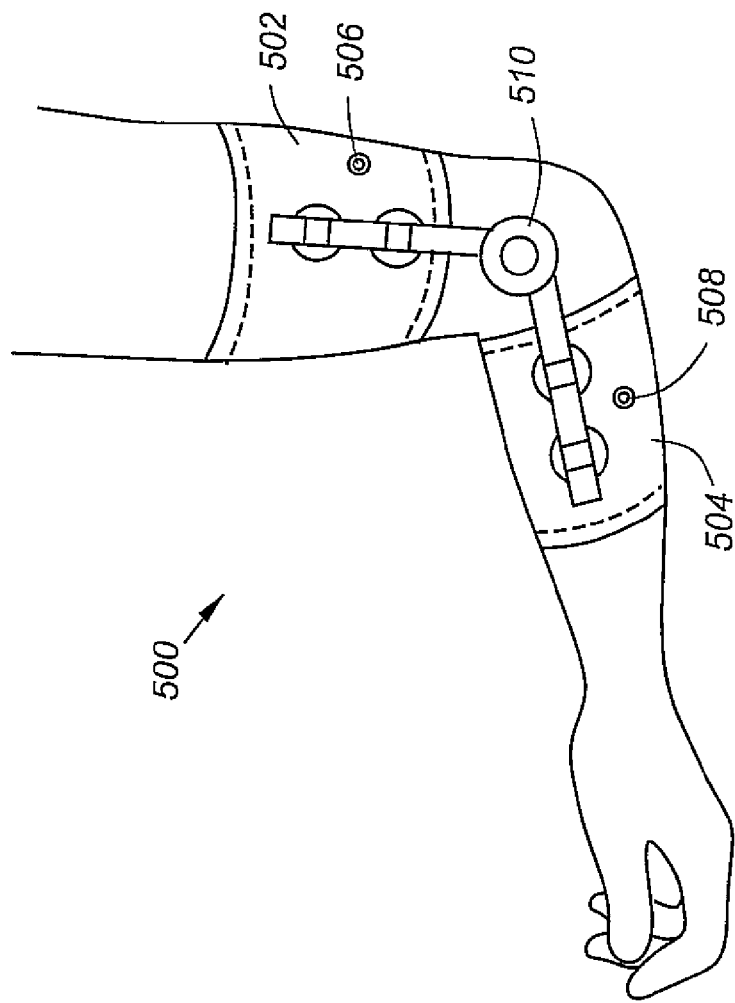
FIG. 5 is a drawing which shows a hinged shoulder orthosis.

FIG. 5 illustrates, generally at 500, an elbow-related embodiment of the invention, having an upper band 502 above the elbow, evacuatable through a port 506, a lower band 504 evacuatable through a port 508, and a hinge mechanism 510.

Figure 6:
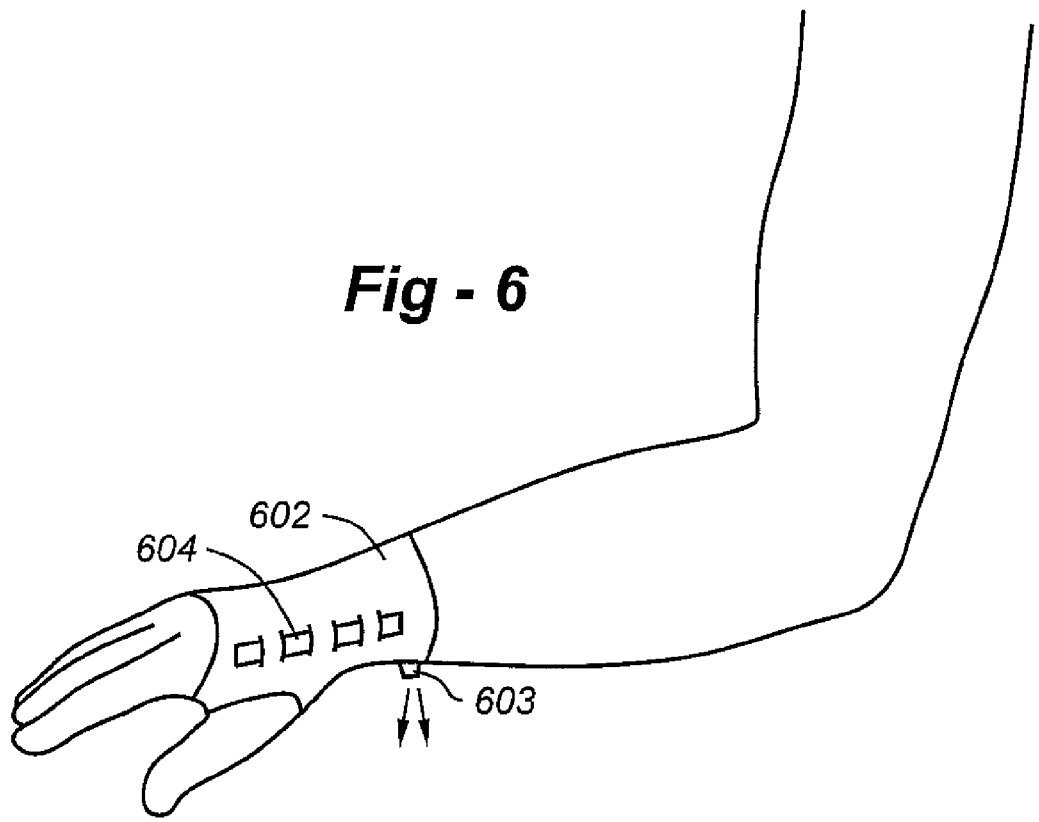
FIG. 6 is a drawing which shows a wrist brace.

FIG. 6 illustrates a wrist brace embodiment, including a sleeve 602, which may or may not be long enough to have one or more finger-receiving apertures, which is evacuatable through a port 603. Although a hinged brace member may be used, FIG. 6 illustrates the use of a single rigid element 604, though additional elements may be used, depending upon the nature of the injury.

Figure 7:
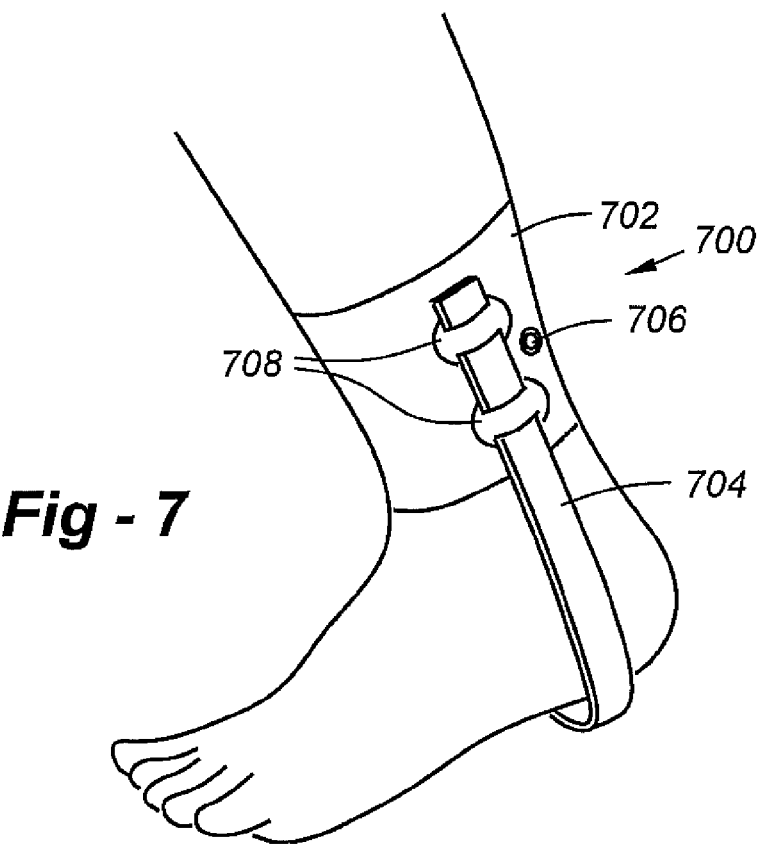
FIG. 7 is a drawing which shows an ankle brace according to the invention.

FIG. 7 illustrates a ankle-related embodiment, depicted generally at 700, including a band 702 evacuatable through a port 706, and a brace member 704 attached to the band 702 at points 708 through any suitable means as discussed elsewhere herein. The advantages of the invention is that, particularly with respect to leg-related and load-bearing applications, once the band or sleeve is evacuated against the skin, so little slippage occurs that the member 704, shown in FIG. 7 allows little if any weight to be applied to the foot, but rather, is applied to the band 702 and distributed to the upper portion of the leg, thereby enabling maladies associated with the foot to heal that much more quickly.

FIG. 8 begins a series of drawings which shows the way in which the invention is applicable to prosthetic as well as orthotic devices, namely, to artificial limbs. FIG. 8, in particular, illustrates the applicability of the invention to an artificial foot or lower leg, including a ground-contacting foot portion 806, having a cavitation to receive the stump of the wearer, above which there is provided a band 802 evacuatable through a port 803. The areas in broken-line illustrated form 810, 812, show that the band 802 can be of any appropriate length of the leg to ensure sufficient weight-carrying capability. The brace member 804, attached to the foot portion 806 at 820 and the band 802 at 822, facilitates weight distribution and equalizes contact between the stump and the cavitation within the lower portion 806. In the event that one or more brace members such as 804 are not required, the top of the prosthesis may simply terminate in an evacuatable member, to hold the prosthesis on without falling off, and without the need for additional rigid elements.

Figures 10, 11, 12:
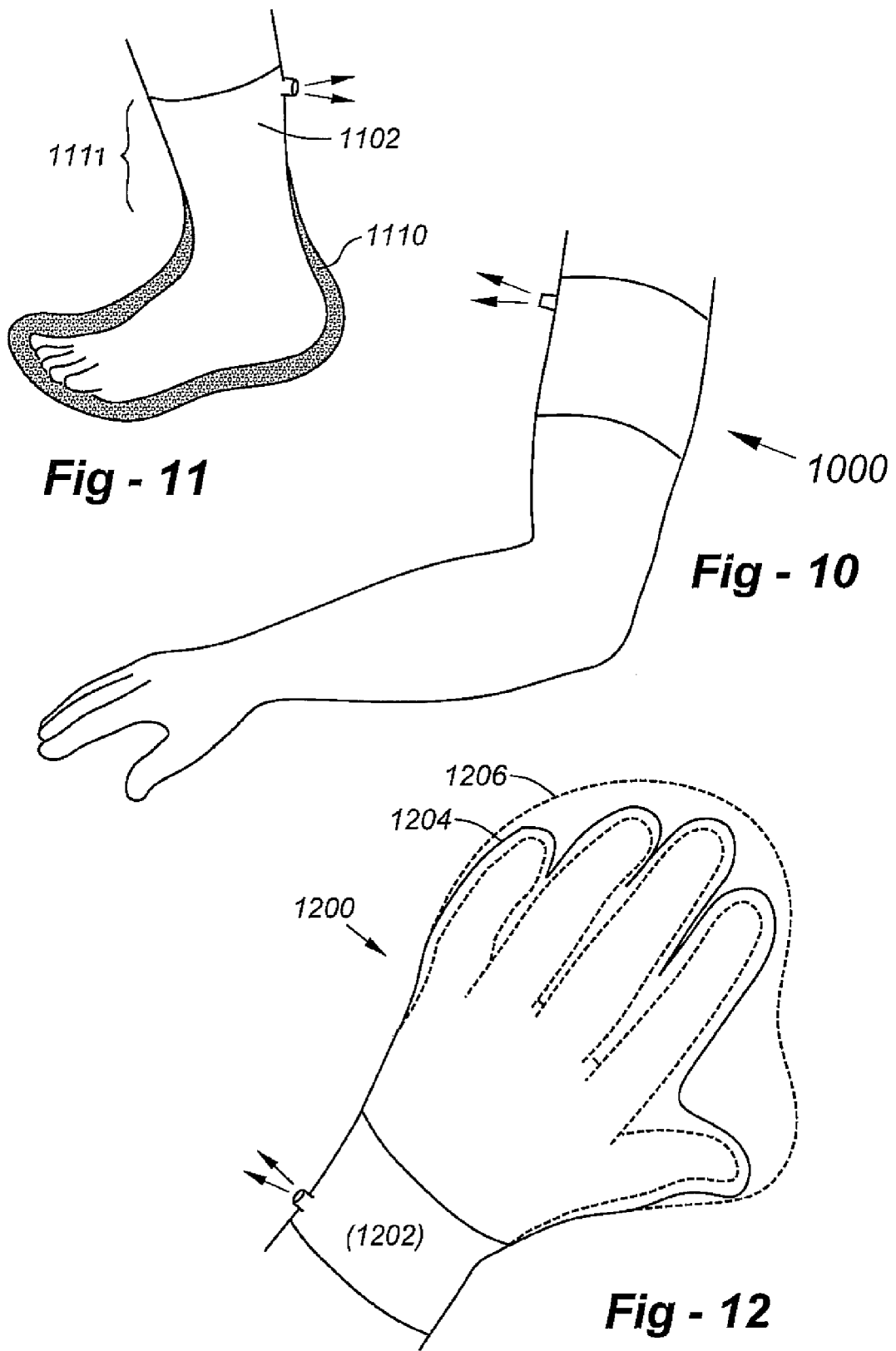
FIG. 10 is a drawing that depicts a longer artificial arm.
FIG. 11 shows the way in which the invention may applied to footwear, with or without insulation or padding.
FIG. 12 illustrates a glove or mitt application.

Such a capability is perhaps better illustrated in FIGS. 9 and 10, which show generally at 900 and 1000, respectively, evacuatable sleeves used to hold on an artificial hand or arm without the need for any additional rigid bracing or hinged members. It can be seen from these drawings, one advantage of the invention is that, in contrast to additional prosthetics which require straps and so forth to encircle the rib cage and/or shoulder area to hold on the prosthesis, due to the tenacious bond between an evacuatable sleeve according to the invention and the skin, such additional fastening mechanisms are no longer required.

In addition to orthotic and prosthetic devices, the invention is applicable to non-medical and non-orthopedic applications, including sport-related gear such as athletic shoes, cross-country and downhill ski boots, gloves and mitts. FIG. 11, for example, shows a foot-covering application, including an evacuatable sleeve 1102 coupled to a layer 1110, which may be used to absorb shock, and/or function as a thermal barrier. For example, in a ski and athletic shoe applications, the evacuatable sleeve may contact the majority of the foot, with the layer 1110 being bonded to the outside of the sleeve for cushioning and/or warmth. Alternatively, the layer may be bonded to the inside of the sleeve or eliminated partially or entirely if the sleeve is evacuated over a stocking, for example. As a further alternative, the use of a vacuum may be limited to a region above the foot, in which case an evacuatable band such as 1111 in FIG. 11 may be provided in conjunction with an otherwise conventional shoe or boot. In some applications, such as cross-country ski boots and swim fins, and the like, the toes may remain exposed for further comfort and flexibility.

FIG. 12 illustrates, generally at 1200, hand-related applications of the invention, taking the form of a glove 1204 or, alternatively, a mitt 1206. Such applications include handball gloves, racquetball gloves, tennis gloves, bicycle/motorcycle gloves, baseball mitts, ski gloves, and so forth. Again, an evacuatable sleeve such as 1202 is used, which may cover the entire hand and be covered a cushioning/thermal layer; cover only the wrist area and be attached to a glove or mitt; or cover the entire hand with the entire hand or portions of the hand such as the palmar surface being covered with a shock-absorbing or thermal barrier layer of material, again, depending upon the ultimate application.

In addition to the use of intermediate or outer layers of material for cushioning, shock-absorbing, or thermal insulation, the invention may utilize an intermediate perforated layer between the evacuatable membrane in the skin, to minimize the overall level of skin compression, thereby improving comfort, particularly for periods of extended wear. Such an intermediate layer may take the form of a honeycomb structure, or other geometric perforation. In terms of the outer fabric or membrane which is evacuated, such a material may be fabricated of a suitable strong and elastic plastics material which is water- and air-impervious. A latex rubber having a thickness on the order of 0.020" more or less is satisfactory for this purpose. Other materials such as synthetic polymer elastomeric films or sheets could also be employed and the film thickness can be varied depending upon the type of material employed.

Figure 13:
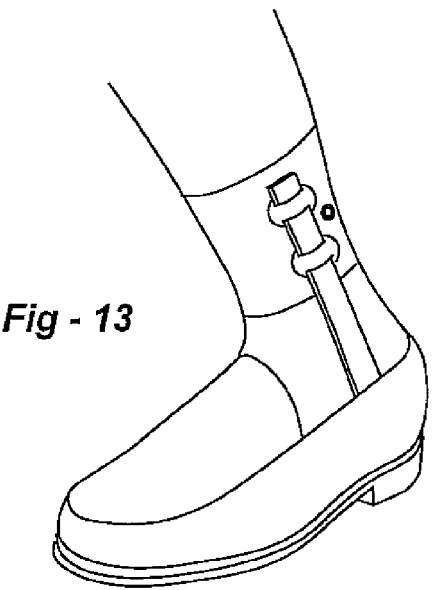
FIG. 13 depicts the rigid structure including a shoe.
Figure 14:
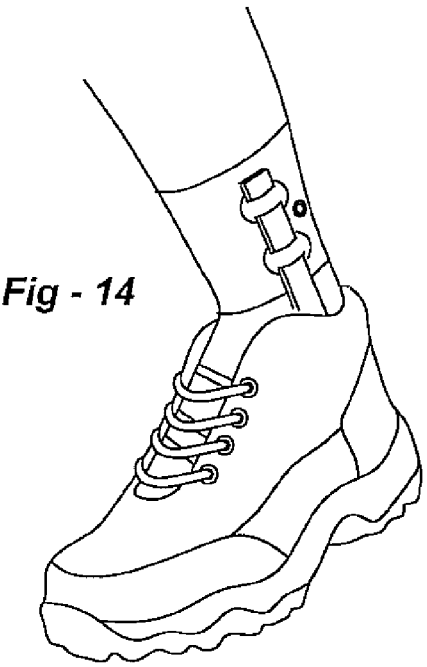
FIG. 14 shows the rigid structure including boot.
Figure 15:
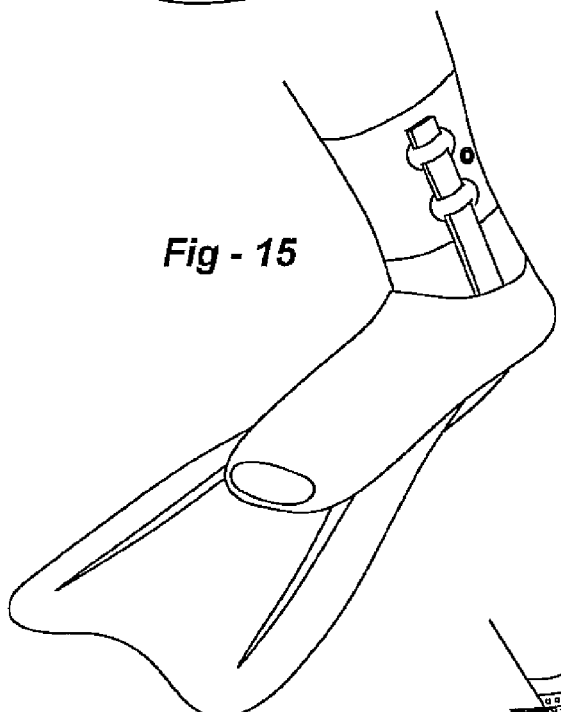
FIG. 15 depicts the rigid structure including a fin.
Figure 16:
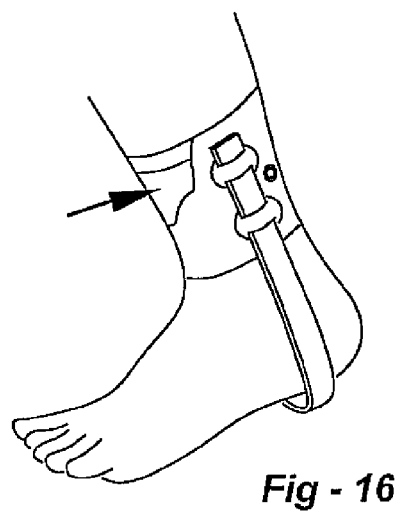
FIG. 16 illustrates an intermediate layer disposed between the inner surface of the band and the skin of a wearer.
Figure 17:
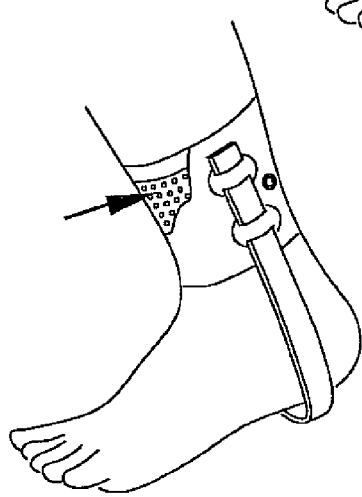
FIG. 17 shows an intermediate perforated layer disposed between the inner surface of the band and the skin of a wearer.

FIG. 13 depicts the rigid structure including a shoe. FIG. 14 shows the rigid structure including boot. FIG. 15 depicts the rigid structure including a fin. FIG. 16 illustrates an intermediate layer disposed between the inner surface of the band and the skin of a wearer. FIG. 17 shows an intermediate perforated layer disposed between the inner surface of the band and the skin of a wearer.

I claim:

1. A body-worn implement, comprising:
   a flexible, continuous band adapted to completely encircle a calf portion of a human leg extending entirely through the band and terminating in an end portion which the band does not cover;
   the band having an inner surface that is initially spaced apart from the skin of a wearer and an outer surface with opposing outer side portions;
   a port in communication with the space between the inner surface of the band and the skin of the wearer, the port facilitating evacuation of the space so that the inner surface of the band makes intimate, slip-free contact with the skin; and
   a rigid structure coupled to the side portions of the band, the rigid structure including a portion that extends around and past the end portion of the leg, thereby transferring loads to the band and calf portion as opposed to the end portion of the leg during ambulation.

2. The implement of claim 1, wherein the rigid structure is permanently or temporarily attached to the side portions of the band.

3. The implement of claim 1, wherein the rigid structure is attached to the side portions of the band using a hook-and-loop fastener.

4. The implement of claim 1, further including an intermediate layer disposed between the inner surface of the band and the skin of a wearer.

5. The implement of claim 1, further including an intermediate, perforated layer disposed between the inner surface of the band and the skin of a wearer.

6. The implement of claim 1, further including a cushioning or thermal-insulating layer inside the band.

7. The implement of claim 1, further including a cushioning or thermal-insulating outside the band.

8. The implement of claim 1, wherein:
   the rigid structure includes a shoe, boot, or fin.

9. The implement of claim 1, wherein the rigid structure includes a cast.

* * * * *

UNITED STATES PATENT AND TRADEMARK OFFICE
CERTIFICATE OF CORRECTION

PATENT NO. : 7,611,476 B2 Page 1 of 1
APPLICATION NO. : 10/791948
DATED : November 3, 2009
INVENTOR(S) : Warren S. Taranow It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 851 days.

Signed and Sealed this

Twelfth Day of October, 2010

David J. Kappos
*Director of the United States Patent and Trademark Office*